United States Patent
Elazar et al.

(10) Patent No.: US 11,903,568 B2
(45) Date of Patent: Feb. 20, 2024

(54) MEDICAL DEVICE HAVING A VALVE FOR AUTOCLAVABILITY

(71) Applicant: DENTAL SMARTMIRROR, INC., Chicago, IL (US)

(72) Inventors: Gidon Oded Elazar, Cohav Yair (IL); Dan Zidkiahu Harkabi, Moshav Lachish (IL); Omri Mordechai Farbstein, Ramat Yishay (IL)

(73) Assignee: DENTAL SMARTMIRROR, INC., Chicago, IL (US)

( * ) Notice: Subject to any disclaimer, the term of this patent is extended or adjusted under 35 U.S.C. 154(b) by 0 days.

(21) Appl. No.: 17/668,283

(22) Filed: Feb. 9, 2022

(65) Prior Publication Data

US 2023/0101078 A1    Mar. 30, 2023

Related U.S. Application Data

(63) Continuation of application No. 17/372,015, filed on Jul. 9, 2021, now Pat. No. 11,278,198.

(51) Int. Cl.
*A61C 1/00* (2006.01)
*A61B 1/247* (2006.01)
(Continued)

(52) U.S. Cl.
CPC ............... *A61B 1/247* (2013.01); *A61B 1/05* (2013.01); *A61B 1/06* (2013.01); *A61L 2/07* (2013.01);
(Continued)

(58) Field of Classification Search
CPC .. A61B 1/247; A61B 1/05; A61B 1/06; A61B 2562/166; A61B 1/00068;
(Continued)

(56) References Cited

U.S. PATENT DOCUMENTS

| 3,830,632 A * | 8/1974 | Guzay | B01D 53/62 128/205.28 |
| 5,951,284 A * | 9/1999 | Lake | A61C 17/08 433/31 |

(Continued)

FOREIGN PATENT DOCUMENTS

| EP | 1550465 A1 | 7/2005 |
| EP | 1574223 A2 | 9/2005 |

(Continued)

OTHER PUBLICATIONS

International Search Report and Written Opinion for International Application No. PCT/US2022/035970, European Patent Office, Netherlands, dated Nov. 25, 2022, 20 pages.

*Primary Examiner* — Howard D Brown, Jr.
(74) *Attorney, Agent, or Firm* — Sterne, Kessler, Goldstein & Fox P.L.L.C.

(57) ABSTRACT

A medical device with a valve for autoclavability is disclosed. The medical device may include a cavity. A channel connects the cavity to an autoclave environment. The channel has a distal end and proximal end. The distal end of the channel may open to the autoclave environment and the proximal end may open to the cavity. A valve may be positioned in or near the channel. The valve may permit gas to flow from the cavity when a pressure inside the cavity is greater than a pressure in the autoclave environment outside the cavity. The valve may also prevent gas from flowing into the cavity when the pressure in the autoclave environment outside the cavity is greater than the pressure inside the cavity.

17 Claims, 9 Drawing Sheets

FIG. 1

(51) Int. Cl.
    *A61B 1/05*         (2006.01)
    *A61L 2/07*         (2006.01)
    *A61B 1/06*         (2006.01)

(52) U.S. Cl.
    CPC ..... *A61B 2562/166* (2013.01); *A61L 2202/24* (2013.01)

(58) Field of Classification Search
    CPC ..... A61B 1/123; A61B 1/0607; A61B 1/0676; A61B 1/24; A61L 2/07; A61L 2202/24; A61C 3/00
    See application file for complete search history.

(56) References Cited

U.S. PATENT DOCUMENTS

| | | |
|---|---|---|
| 9,585,549 B1 | 3/2017 | Elazar et al. |
| 9,655,504 B1 | 5/2017 | Elazar et al. |
| 11,278,198 B1 | 3/2022 | Elazar et al. |
| 2020/0179548 A1* | 6/2020 | Anani ........................ A61L 2/24 |

FOREIGN PATENT DOCUMENTS

| | | | |
|---|---|---|---|
| JP | 2000107120 A | 4/2000 | |
| JP | 2002330921 A | 11/2002 | |

* cited by examiner

MEDICAL DEVICE HAVING A VALVE FOR AUTOCLAVABILITY

BACKGROUND

Field

The present disclosure relates to sealing medical devices, and particularly dental devices, during an autoclave procedure.

Technical Background

An autoclave is a common device in medical and dental offices. The autoclave sterilizes medical and dental instruments using extreme temperatures and pressures to kill bacteria, viruses, fungi, spores, and other contaminants. The temperatures and pressures may vary throughout the autoclave procedure. For example, at the beginning of the autoclave process, the temperature in the autoclave may rise to in excess of 110 degrees Celsius while removing air from the chamber. Typically, pressurized saturated steam at 121° C. (250° F.) is applied in the chamber for around 15-20 minutes depending on the size of the load and the contents. At the end of the autoclave process, the temperature and pressure in the autoclave may be restored to approximately the temperature and pressure of the environment of the autoclave (for example, on the counter of a dentist's office). Instruments may be removed from the autoclave chamber before fully cooling off, thus settling of the autoclave process may occur outside the chamber.

Air removal may be accomplished in a variety of ways. Gravity displacement autoclaves, also called gravity autoclaves, inject steam into the autoclave chamber and then rely on that steam, which is heavier than air, to force the air to leave the chamber through the drain vent at the bottom. Prevacuum or prevac autoclaves use a vacuum pump to remove air from the chamber before steam is admitted to it, which means that steam penetrates even porous objects almost instantly.

One instrument that is often autoclaved is an intraoral mirror. Intraoral mirrors, also known as mouth mirrors or dental mirrors, are among the most functional and frequently used of dental instruments. Viewing objects in a mouth directly is difficult due to a limited, or perhaps nonexistent, line of sight. Intraoral mirrors allow a health care provider (HCP), for example dentist, hygienist and others, to indirectly view teeth and other objects in a patient's mouth, such as the patient's gums and tongue, by observing their reflections in a mirror. Health care providers use the intraoral mirror for a variety of tasks, including, but not limited to, evaluation and diagnosis, treatment selection, and even to assist the treatment itself. A health care provider may use other tools, such as a dental hand piece, in conjunction with the mirror to conduct procedures, such as tooth preparation, when the procedures are conducted in areas that are not directly visible.

Not only are they used as a visual aid, intraoral mirrors are also used as rigid tools to manipulate or protect objects in a patient's mouth. For example, a health care provider may use an intraoral mirror to shift a patient's cheek to make space for treatment or to expand the mouth space for improved visibility. In addition, an intraoral mirror can protect soft and hard tissue structures of a patient's mouth while other parts of the mouth are treated.

Since an intraoral mirror is in contact with a patient's tissues inside their mouth, the mirror must be sterilized before each treatment. Most intraoral mirrors are made almost entirely of glass and metal. So, they can withstand the autoclaving process. Only after many use-and-sterilization cycles does the mirror eventually lose some of its clarity and its reflectiveness, thus needing replacement.

Dental mirrors may exist that have electronic components such as a camera and light emitting diode (LED) lights connected through a printed circuit board (PCB). One such dental mirror is described in U.S. Pat. No. 9,655,504, incorporated by reference herein. Electronic components may be sensitive to temperature and particularly moisture. If water condenses on a PCB, it can cause the PCB to short circuit. Optical components can also become damaged if exposed to too much heat, pressure, or moisture. For these reasons, these mirrors are often not autoclaved, instead needing other methods of sterilization, such as submerging in disinfectant liquid or covering with a single-use disposable sleeve.

Additionally, while medical devices are typically sealed where portions are joined, these seals may contribute to issues during the autoclave process. Specifically, while airtight seals may prevent air, liquid, and vapors from entering the sealed cavity, it also prevents gas from escaping from the cavity. This creates a small air pocket. This small air pocket can cause damage to the medical device as the pressure outside the medical device changes. For example, if the pressure in the air pocket of a medical instrument becomes substantially larger than the pressure in the cavity, it may force components to detach from the instrument or may cause components inside to collapse if they cannot sustain the pressure. An air pocket in an airtight sealed cavity has a significant probability that its pressure will rise substantially while the autoclave chamber rises in temperature.

What is needed is an effective device that is sealed to gas, withstanding substantial pressure despite having an air pocket, while limiting the rise in the pressure of the air pocket in a controlled manner.

SUMMARY

There is a need for a low cost, effective element that seals while preventing damaging pressure from building in portions of a medical or dental instrument.

According to some embodiments, a medical device includes a cavity. A channel may be formed in the medical device between the cavity and an autoclave environment. The autoclave environment may be, for example, the interior of an autoclave device, specifically, while the autoclave device is in operation. The channel may have a proximal end that opens to the cavity and a distal end that opens to the environment. A valve may be fluidly connected to the channel and may be capable of sealing the channel. The valve permits gas to flow from the cavity of the dental instrument when a pressure inside the cavity is greater than a pressure in the autoclave environment outside the cavity. The valve may prevent gas from flowing into the cavity when the pressure in the autoclave environment outside the cavity is greater than the pressure inside the cavity.

In some embodiments, the valve includes a piston rod that extends into the channel. A sealing member may be connected to the piston rod. The spring may bias the piston rod in the proximal direction.

In some embodiments, the medical device includes a printed circuit board. The printed circuit board may be disposed in the cavity. The cavity may also include an image sensor operatively coupled to the printed circuit board. The image sensor may also be inside the cavity. In some embodiments, a light source is operatively coupled to the printed circuit board. The light source may be inside the cavity.

An indicator may also be included. The indicator may be configured to indicate a pressure difference between a pressure in the environment and a pressure in the cavity. In this sense, the environment may be considered more broadly than just the environment of the autoclave. For example, the environment may be outside the autoclave—such as a medical or dental office generally. The indicator may be coupled to the sealing member. In some embodiments, the indicator indicates a pressure difference between the pressure in the environment and the pressure in the cavity by being located at one of a first and a second position.

According to some embodiments, a dental instrument has a channel having a distal and a proximal end. The proximal end is configured to engage a cavity of the dental instrument. A release plug may be located in the channel. The release plug may include a sealing member coupled to a piston rod. The piston rod is biased in the proximal direction by a spring. The release plug permits gas to flow from the cavity of the dental instrument when a pressure outside the dental instrument decreases below the pressure of the air pocket or equivalently the pressure of the air pocket increases above the pressure outside during the autoclave process. The release plug also prevents gas from flowing into the cavity of the dental instrument when the outside pressure increases above the pressure of the air pocket or equivalently the pressure of the air pocket decreases below the pressure outside during the autoclave process.

According to some embodiments, a plug may be for use with a dental instrument during an autoclave procedure. The plug may include a hollow housing having a distal and a proximal end. The proximal end may be configured to engage a cavity of the dental instrument. A release plug may be located in the hollow housing. The release plug may also be hollow. The release plug may include a valve. The valve may operate so as to permit gas to flow from the cavity of the dental instrument when a pressure outside the cavity decreases relative to the pressure inside the cavity. The valve may also operate so as to prevent gas from flowing into the cavity of the dental instrument when the pressure outside increases relative to the pressure inside the cavity. The valve may include a piston rod with a sealing member and may be partially within the hollow portion of the release plug. The piston rod may be coupled to a spring, which may bias the rod in the proximal direction.

The plug may include an indicator. The indicator may be configured to indicate a pressure difference between the pressure outside and a pressure inside the cavity. For example, the indicator may be in a first position when there is no or little pressure difference between inside the cavity and outside. The indicator may be in a second position when there is a pressure difference between inside the cavity and outside. In some embodiments, the first position may be more distal from the second position. This may make the first position more visible in the hollow release plug. The indicator may be coupled to or formed on the sealing member.

In some embodiments, a plug may include a hollow cylindrical housing having an outer surface, an inner surface, a proximal end, and a distal end. A gasket may be positioned in a groove formed on the outer surface of the housing. The gasket may aid in sealing the cavity. An end piece may be coupled to the distal end of the housing. The end piece may have a void that is aligned with the hollow portion of the housing. A release plug may be mated with the inner surface of the hollow portion of the housing. The release plug may include a hollow cylindrical body having a proximal end and a distal end. A first and a second location may be identified along the axis of the hollow portion of the release plug. The first location may be distal to the second location. A piston rod may be located and move axially through a portion of the hollow cylindrical body.

A spring may be located around the piston rod. The spring may apply a spring force to the piston rod in the proximal direction. A sealing member may be coupled to the distal end of the piston rod, interior of the hollow cylindrical body. The sealing member permits gas to flow from the cavity of the dental instrument when a pressure inside the cavity is greater than a pressure in the environment outside the cavity. The sealing member may prevent gas from flowing into the cavity when the pressure in the environment outside the cavity is greater than the pressure inside the cavity.

An interior of the hollow portion of the housing may have more than one section. For example, the hollow portion of the housing may have a first section, a second section, and a third section. Each of the sections may have a different diameter to accommodate different components. For example, the third section may have a diameter that is greater than the diameter of the second section, and the second section may have a diameter that is greater than the diameter of the first section. The first section may be distal to the second section, which may be distal to the third section. In some embodiments, a second gasket may be positioned in a second groove formed on the outer surface of the housing. This second gasket may further seal the cavity of a medical or dental instrument. The release plug may also include a release gasket that helps to seal the release plug in the hollow portion of the housing.

An indicator may be located on the distal end of the sealing member. When a distal pressure is greater than a proximal pressure, the sealing member may be proximally displaced. The release plug may be mated to the housing with a threaded connection.

According to some embodiments, a medical device may include a cavity. A channel having a sealing member may connect the cavity and an environment outside the cavity. The sealing member permits gas to flow from the cavity of the medical device when a pressure inside the cavity is greater than a pressure in the environment outside the cavity. The sealing member may prevent gas from flowing into the cavity when the pressure in the environment outside the cavity is greater than the pressure inside the cavity.

According to some embodiments, the sealing member may be a one-way valve. In some embodiments the medical device may be an intra-oral mirror. The medical device may also comprise an image sensor located inside the cavity. The image sensor may be operatively connected to a connector. The connector may be configured to receive a streamer. The streamer may be a removable component that is not able to be autoclaved.

According to some embodiments, a medical device includes a cavity. A channel may be formed in the medical device between the cavity and an environment. The environment may be, for example, an autoclave device. The channel may have a proximal end that opens to the cavity and a distal end that opens to the environment. A first and a second location may be defined along an axis of the channel. The first location may be distal to the second location. A piston rod may extend into the cavity. A sealing member may be connected to the piston rod interior of the channel. A spring biases the piston rod in the proximal direction. The force provided by the spring is sufficient to hold the sealing member at the second location as long as the pressure inside the cavity is not greater than the pressure of the environment, with an addition of a threshold.

According to some embodiments, when the sealing member is at the first location, the sealing member permits the flow of air through the channel. And, when the sealing member is at the second location, the sealing member prohibits the flow of air through the channel. Additional features and advantages of the processes and systems described herein will be set forth in the detailed description which follows, and, in part, will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings.

Figure 1:
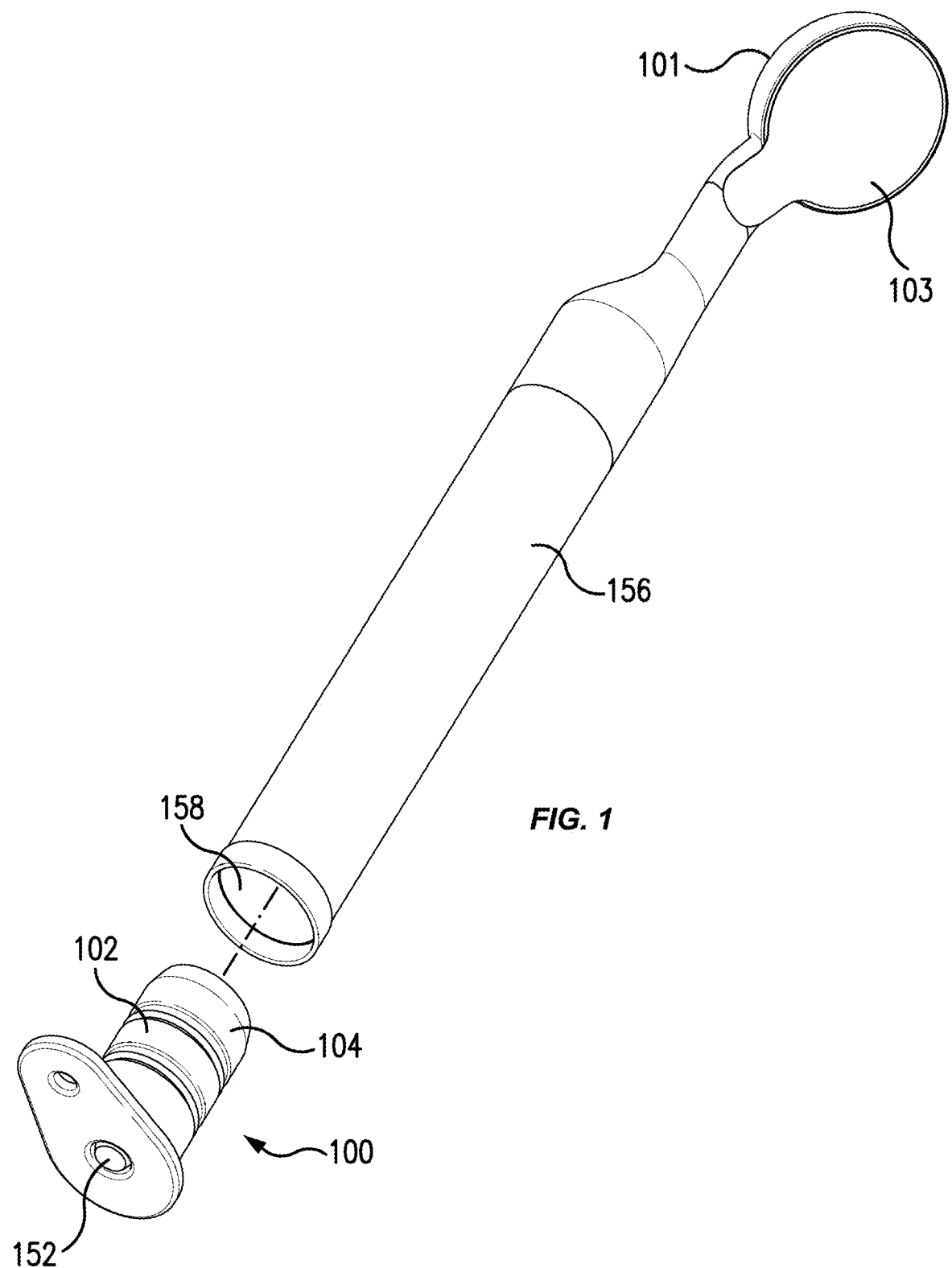
FIG. 1 is a diagram illustrating components of a plug with a valve and a dental mirror.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. Additionally, generally, the left-most digit(s) of a reference number identifies the drawing in which the reference number first appears. Unless otherwise indicated, the drawings provided throughout the disclosure should not be interpreted as to-scale drawings.

DETAILED DESCRIPTION

As described above, while the extreme temperature and pressure changes may be instrumental in autoclaving medical and dental devices, the changes in temperature and pressure may also damage certain medical and dental instruments. For example, some medical or dental instruments may have internal cavities. The internal cavity of a medical or dental tool may contain an air pocket. When the pressure and temperature changes in the autoclave, the air pocket may apply unexpected pressures to the medical or dental instruments in the autoclave.

The air pocket may be near these internal components. For example, if a dental mirror's reflective surface is seated in a housing, and the air pocket may be behind the reflective surface in the housing. That air pocket may be at or near atmospheric pressure before the autoclave process. During the autoclave process, the difference in the air pressure in the autoclave and the air pressure of the pocket may exert a force on the mirror in the housing. If the air pressure difference between the autoclave environment and the air pocket is sufficiently large, the resulting force on the mirror may force the mirror from the housing, damaging the dental mirror.

An autoclave process, and its effects on a medical device will be described in detail with examples. When the medical device enters the autoclave, a pressure of an autoclave environment and the pressure of the air pocket are equal (approximately, 1 atmosphere, for example). When the autoclave process begins, the temperature may first rise. This heats the medical device raising the pressure of the air pocket. Thus, the stresses on medical device may be from both internal pressure and expansion. According to disclosed embodiments, the increased pressure from the air in the air pocket is reduced by allowing air to exit through a valve. As the autoclave process continues, there is a race between the rising pressure of the autoclave environment and the rising pressure of the air pocket. By allowing air to exit through the valve, the internal forces due to the pressure difference are controlled. When the autoclave process reaches an equilibrium, temperature is uniform (for example, 134C) and the pressure is uniform or close to uniform (for example, 2 atmospheres) among the autoclave and the medical device. Not that the pressure of both the air pocket and the autoclave environment are equal at this point due to the temperature rise in the autoclave.

As the autoclave process concludes, the autoclave environment pressure and temperature decrease. While the pressure of the autoclave environment decreases, the pressure of the air pocket may decrease more slowly due to the retained heat. Accordingly, the valve will permit air to exit the air pocket. Eventually, near the end of the cycle, the pressure of the autoclave environment decreases to 1 atmosphere. As the medical device cools, the pressure of the air pocket continues to drop and eventually may drop below the environment pressure. If the valve is coupled to a plug, this may result in some small effort to remove the plug. According to an embodiment, a valve allows air to escape from the air pocket when air is removed from the autoclave chamber or the pressure difference is high because of the heating of the air inside the cavity. However, the valve also prevents moisture from the steam from entering the air cavity and possibly damaging electronic components therein. Reference will now be made in detail to embodiments of plugs for medical and dental instruments, examples of which are illustrated in the accompanying drawings.

As illustrated in FIG. 1, plug 100 is configured to engage with a dental instrument 156. Dental instrument 156 may be at least a portion of a smart dental mirror device. For example, dental instrument 156 may have a reflective surface 101 that a health care provider may use to view the interior of the patient's mouth. Reflective surface 101 may be made of an optical substrate configured to reflect light, such a glass or sapphire. Reflective surface 101 is also referred to as a viewfinder mirror, as it may be used as a viewfinder directing the capture of desired images in the patient's mouth.

Dental instrument 156 has a cavity 158 formed in one side of dental instrument 156. As will be described below, dental instrument 156 may house electronic components, such as an image sensor, lights, and control circuitry, that may fail if exposed to pressure, moisture, and steam. And yet, according to embodiments, dental instrument 156 may be autoclavable. As will be also discussed below, cavity 158 may be configured to engage with another component, called a streamer, which houses electronic components that are not subject to autoclaving.

In some embodiments, dental instrument 156's cavity 158 is fluidly connected with internal areas of dental instrument 156. These internal areas are where electronic components are housed. To allow for fluid connection, a pin hole (not shown) may exist that allows gases, such as air and steam, to transit between cavity 158 and the internal areas. These internal areas also may be where known or expected air pockets form. For example, it may be known that an air pocket may form behind the mirror of a dental mirror, where several control circuitry and other components are housed. Thus, a volume behind the mirror may be fluidly connected to cavity 158. This fluid connection may be, for example, a small hole forming a passage for the air pocket, or may be one or more valves or pumps to control the movement of air from the known or expected air pocket into cavity 158. A diaphragm may also be included to reduce the moisture flow while still permitting gas flow.

In the absence of this small hole, dental instrument 156 may have an air pocket behind reflective surface 101. When the pressure in the autoclave machine drops (or the temperature increases), a difference between a pressure within the air pocket and in the autoclave chamber may dislodge reflective surface 101. Because the air pocket behind the mirror is fluidly connected to cavity 158, the air in the air pocket can escape from the dental instrument 156 through the cavity.

While allowing escape during the pressure drop, the small hole also may allow steam to enter the device when dental instrument 156 is autoclaved. The steam can cause electronic components within dental instrument 156 to fail. To avoid this, in some embodiments, dental instrument 156's cavity 158 may be sealed by plug 100. Plug 100 may serve multiple functions. For example, plug 100 may seal cavity 158 to prevent particles, steam, or other contaminants from entering cavity 158 and hence the interior of dental instrument 156. Plug 100 may also act as a one-way valve to permit the release of pressure from inside cavity 158 during the autoclave process. Although not shown in FIG. 1, in alternative embodiments, the one way valve in plug 100 may be built into dental instrument 156, avoiding the need for a hole to allow fluid connection between cavity 158 and the interior of dental instrument 156.

According to some embodiments, plug 100 has housing 102. Housing 102 may be formed of any number of materials, including, for example, stainless steel. Housing 102 may be shaped to fit tightly into a void of cavity 158. For example, if the opening to cavity 158 is circular, housing 102 may also be circular. Housing may have a proximal end 120 and a distal end 122. Housing 102 has a housing outer surface 104 and a housing inner surface 106. One or more grooves 126 may be formed in housing outer surface 104.

Figure 3:
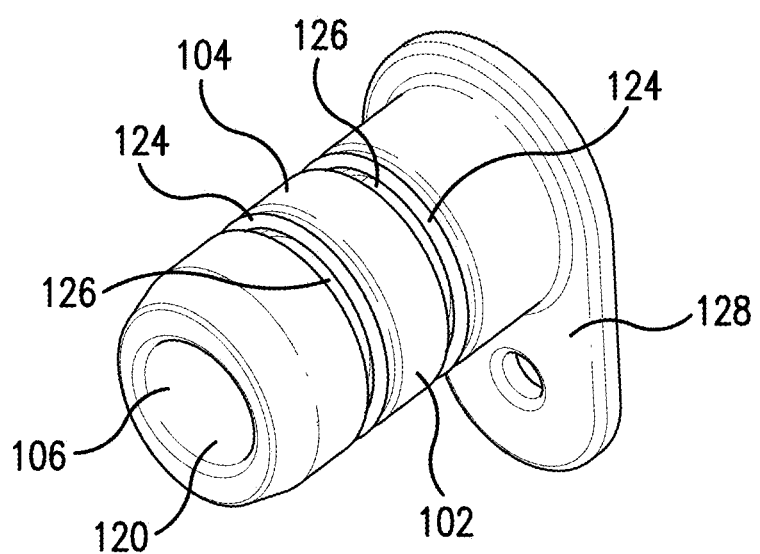
FIG. 3 is another diagram illustrating the plug.

Grooves 126 may be shaped to receive gaskets 124 as shown in FIG. 3. Gaskets 124 help to provide an airtight seal for cavity 158.

According to some embodiments, housing 102 may have inner surface 106. Inner surface 106 may be configured to receive additional components, as illustrated in the cross section in FIG. 4. For this purpose, inner surface 106 may have components that mate with additional components. For example, inner surface 106 may have treaded surfaces. In some embodiments, inner surface 106 of housing 102 may have different sections.

Figure 4:
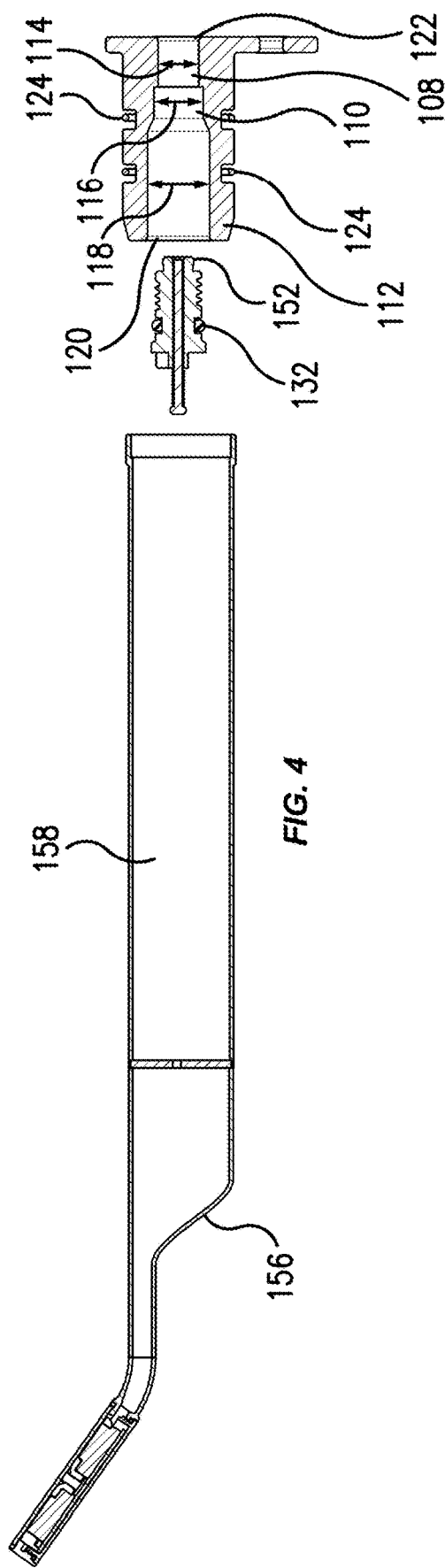
FIG. 4 is a cross section view of the plug of FIG. 3.
Figure 5:
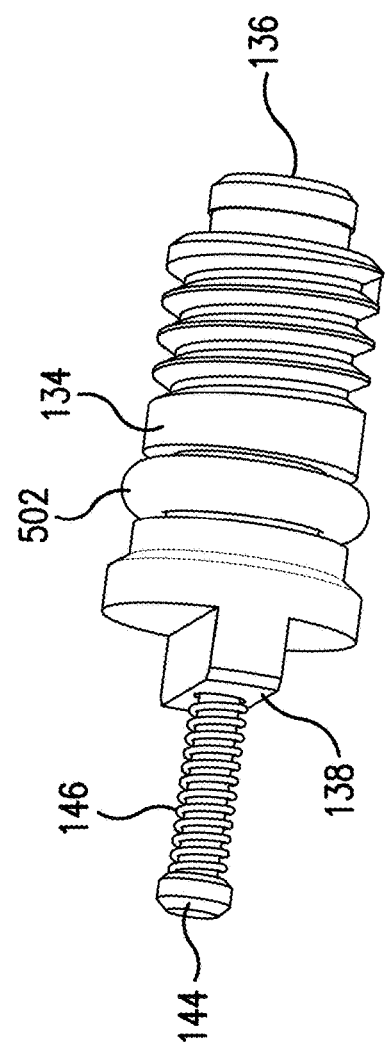
FIG. 5 is a diagram of a release plug.

For example, as illustrated in FIG. 4, housing 102 may have a first section 108, a second section 110, and a third section 112. Each section may have a different size or shape. For example each of first, second, and third sections may be circular and have a first section diameter 114, a second section diameter 116, and a third section diameter 118, respectively. The various sections may be shaped to aid in the placement of different components on the interior of housing 102. For example, first section diameter 114 may be less than second section diameter 116, which may be less than third section diameter 118. In this way, an object inserted into housing 102 may be funneled to the proper location. Gasket 502 may be positioned to rest at the position where the second and third sections meet.

Figure 2:
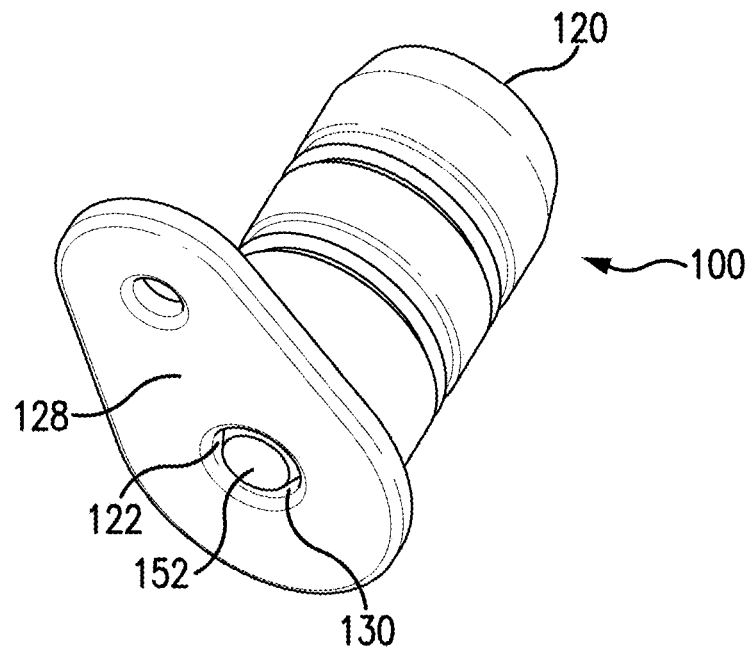
FIG. 2 is a diagram illustrating the plug.

As shown, for example, in FIGS. 2 and 3, an end piece 128 may be located at the distal end of plug 100. This may be a flat surface protruding radially from the dental mirror that aids in handling or storing plug 100. An end piece void 130 may be formed in end piece 128. End piece void 130 may permit plug 100's housing 102 to permit fluid communication with the environment, such as the environment of an autoclave and cavity 158.

According to some embodiments, plug 100 includes a release plug 132. Release plug 132 may be configured to be coupled to housing 102 by engaging housing inner surface 106. For example, release plug 132 may be coupled to housing inner surface 106 using a threaded connection. In some embodiments, release plug 132 may be formed as one piece with plug 100.

Release plug 132 operates as a one-way valve. Release plug 132 permits higher pressure air from inside cavity 158 to escape from cavity 158 during the autoclave process but prevents air (and steam) from re-entering cavity 158. Release plug 132 includes a hollow cylindrical body 134 through which the air may escape. Release plug 132 may have a proximal end 136 and a distal end 138. A piston rod 144 may be inserted in hollow cylindrical body 134. A sealing member 184 may be located at the distal end of piston rod 144 and may seal hollow cylindrical body 134. A spring 146 may be coupled to the proximal end of piston rod 144 and may bias piston rod 144 in the proximal direction. An indicator 152 may be coupled to the distal end of sealing member 184. Indicator 152 may be a visual indicator, for example a different colored segment.

Release plug 132's hollow cylindrical body 134 may also include a first position 140 and a second position 142. First position 140 may be distal of second position 142.

Figure 6A:
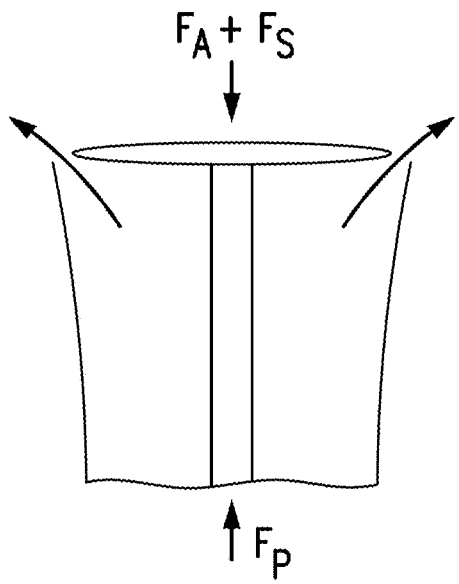
FIGS. 6A-6C are a schematic illustrating the operation of the plug according to some embodiments.
Figure 6B:
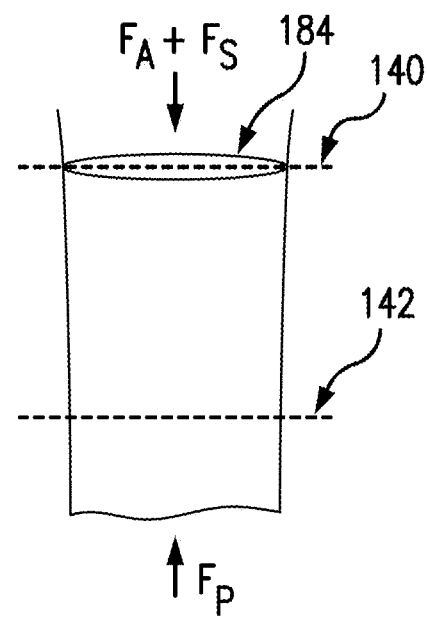
Figure 6C:
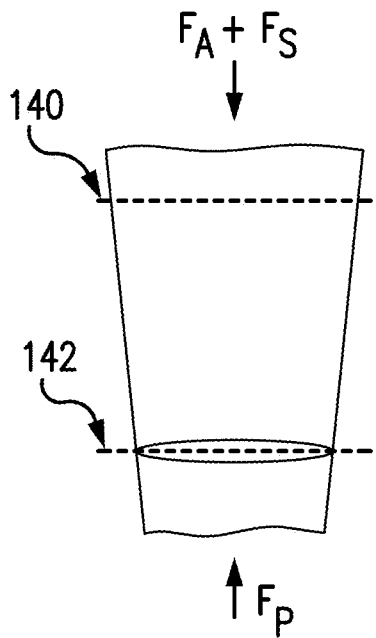

FIGS. 6A-6C show a schematic representation of release plug 132's operation. Each figure shows sealing member 184 coupled to piston rod 144. A proximal opening Op is fluidly coupled to cavity 158. A distal opening Od is fluidly coupled (i.e. open) to the environment of the autoclave device. The operation of release plug 132 is best understood with reference to the forces acting on sealing member 184 during the autoclave procedure. As previously mentioned spring 146 biases sealing member 184 in the proximal direction. Thus, spring 146 applies force Fs in the proximal direction. The pressure difference between the pressure in cavity 158 and the environment of the autoclave also applies a force to sealing member 184. The magnitude and direction of the force is dependent on the difference in the pressure in cavity 158 and the environment of the autoclave. The pressure in the autoclave environment, Pa, may result in a force, Fa, on sealing member 184. For example, when the pressure Pa in the autoclave is greater than the pressure in the cavity, sealing member 184 may have a resulting force in the proximal direction. When the pressure in the autoclave is less than the pressure in the cavity, the force on sealing member 184 is in the distal direction.

The relevant forces on sealing member 184 can thus be summarized as F=(Fp−Fa)−Fs, where (Fp−Fa) is the force from the difference in the pressures (Pp−Pa)*(area of sealing member 184), Pp is the pressure in the cavity, and Fs is the force of the spring. In FIGS. 6A-6C, forces Fa and Fp are shown to represent pressure forces in the different directions. The resulting force from the pressure difference could be in either the proximal or the distal direction, depending on the pressure difference. Additional forces may also be present but are not shown. For example, there may be additional normal forces to the surfaces of sealing member 184 as it moves in the channel.

Components adjacent to the cavity may be sensitive to forces exerted by the pressure in the cavity. For example, if a mirror seals the cavity, the mirror may be unable to withstand a force in excess of 0.5 kgf. If, for example, the mirror has an area of 3.14 $cm^2$, the pressure in the cavity should not exceed 0.16 Bar above the pressure of the environment (Force (kgf)=Pressure (Bar)*Area ($cm^2$)). This may be considered the maximum permitted pressure difference. To avoid the over pressure, the valve should release pressure from the cavity before the maximum permitted pressure difference is reached. If a spring is used as part of the valve, for example, the spring force should be calibrated appropriately. For example, if the sealing member has an area of 0.125 $cm^2$, the spring should be calibrated to provide a force of no more than 0.02 kgf when extended to a point to permit gas to exit the cavity. This is calculated, for example, by multiplying the maximum permitted pressure difference by the area of the sealing member.

FIG. 6A shows sealing member 184 during the process of the autoclave procedure where the pressure in the autoclave drops. At this point, the forces acting on sealing member 184 drive sealing member 184 in the distal direction because the pressure inside cavity 158 is greater than the pressure in the autoclave. Once sealing member 184 is sufficiently displaced, air trapped in cavity 158 is allowed to escape into the autoclave. This begins to equalize the pressure between the autoclave environment and cavity 158. As the pressure begins to equalize, sealing member 184 moves in the proximal direction because the spring force dominates.

FIG. 6B shows sealing member 184 at a first position 140. At this position, cavity 158 remains sealed, but is on the verge of allowing more air to exit cavity 158. Thus, if pressure continues to drop in the autoclave (or equivalently, raise in the cavity), sealing member 184 will move distally from first position 140 to permit more air to exit from cavity 158.

FIG. 6C shows sealing member 184 at a second position 142. As previously mentioned, second position 142 is proximal (i.e. closer to cavity 158 when in use) than first position 140. As the pressure rises in the autoclave during the autoclave process, the increased force drives sealing member 184 to second position 142. At the end of the autoclave procedure, when the pressure in the autoclave is equal to atmospheric pressure and the temperature dropped to room temperature, the pressure in cavity 158 should be approximately the lowest pressure experienced during the autoclave procedure. In some procedures, this is lower than the environment pressure. Accordingly, sealing member 184 is held in second position 142 by the combined force of spring 146 and the higher pressure of the outside environment.

An indicator 152 may be on the distal end of sealing member 184. Indicator 152 may be, for example, a painted feature, sticker, reflector, or other indicator. Indicator 152 may aid the operator in confirming that the autoclave procedure adequately sterilized the medical device and may also confirm that the medical device is not damaged.

As previously mentioned, after the autoclave procedure, the pressure in cavity 158 should be low compared to the pressure of the surrounding environment. Thus, indicator 152 should be mostly obscured because it is located at second position 142. However, if, after the autoclave procedure, indicator 152 is visible (or, in some embodiments, prominently visible), the auto clave procedure may have failed. Alternatively, plug 100 may have failed to adequately seal cavity 158, or the medical instrument coupled to plug 100 may be cracked such that cavity 158 is in fluid connection with the environment of the autoclave device. This may indicate to the operator that the medical device requires repair or replacement.

Figure 7:
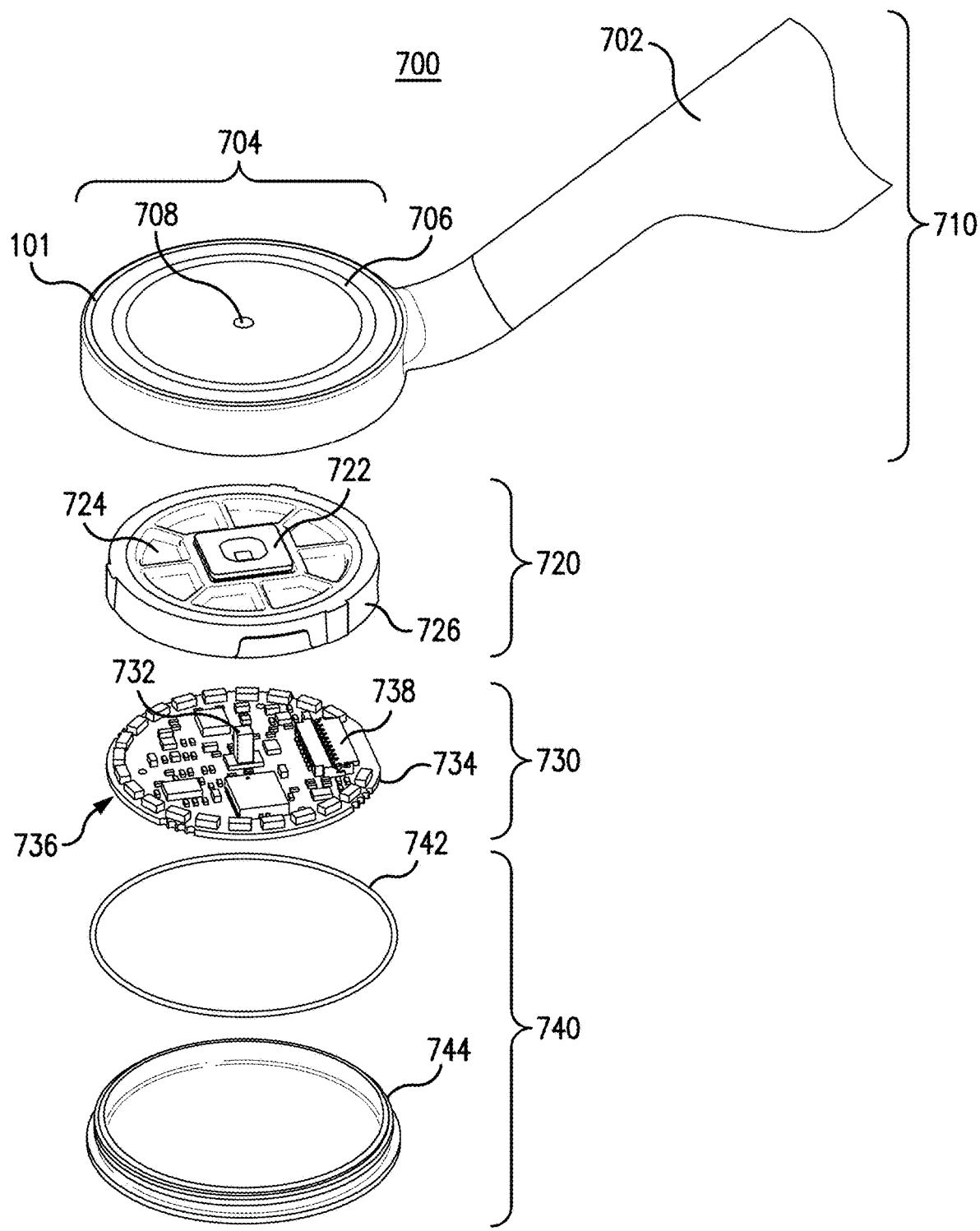
FIG. 7 illustrates a breakout diagram showing a head portion of a dental mirror.

FIG. 7 illustrates a breakout diagram showing assembly of a head portion of a dental mirror. As discussed above, dental instrument 156 includes an internal cavity that includes electronic components. The internal cavity and electronic components are illustrated in diagram 700 in FIG. 7.

Assembly of the head component involves four layers of components: layer 710, layer 720, layer 730, and layer 740. Layer 710 includes a mirror head 704 and a handle 702 connected to each other. Mirror head 704 includes reflective surface 101, a pass-through 708, and a pass-through 706.

Pass-through 708 allows the pass-through of light or visual information to allow light or visual information to reach an image sensor 732 (so that a respective image can be captured). Pass-through 706 allows light from light sources 736 to exit mirror head 704. In some embodiments, pass-throughs 706 and 708 are an opening in reflective surface 101. In some embodiments, pass-throughs 706 and 708 are a transparent or semi- or partially-transparent area in reflective surface 101. In some embodiments, pass-throughs 706 and 708 include an optical lens. Pass-throughs 706 and 708 is a section of the area of reflective surface 101 that becomes transparent or partially transparent when light, possibly of an intensity above some threshold, is present. In some embodiments, pass-throughs 706 and 708 are a section of the area of reflective surface 101 that becomes transparent or partially transparent when electrical current or voltage is present. Pass-throughs 706 and 708 can be located at the center of or at the perimeter, or at other locations of reflective surface 101.

Figure 8:
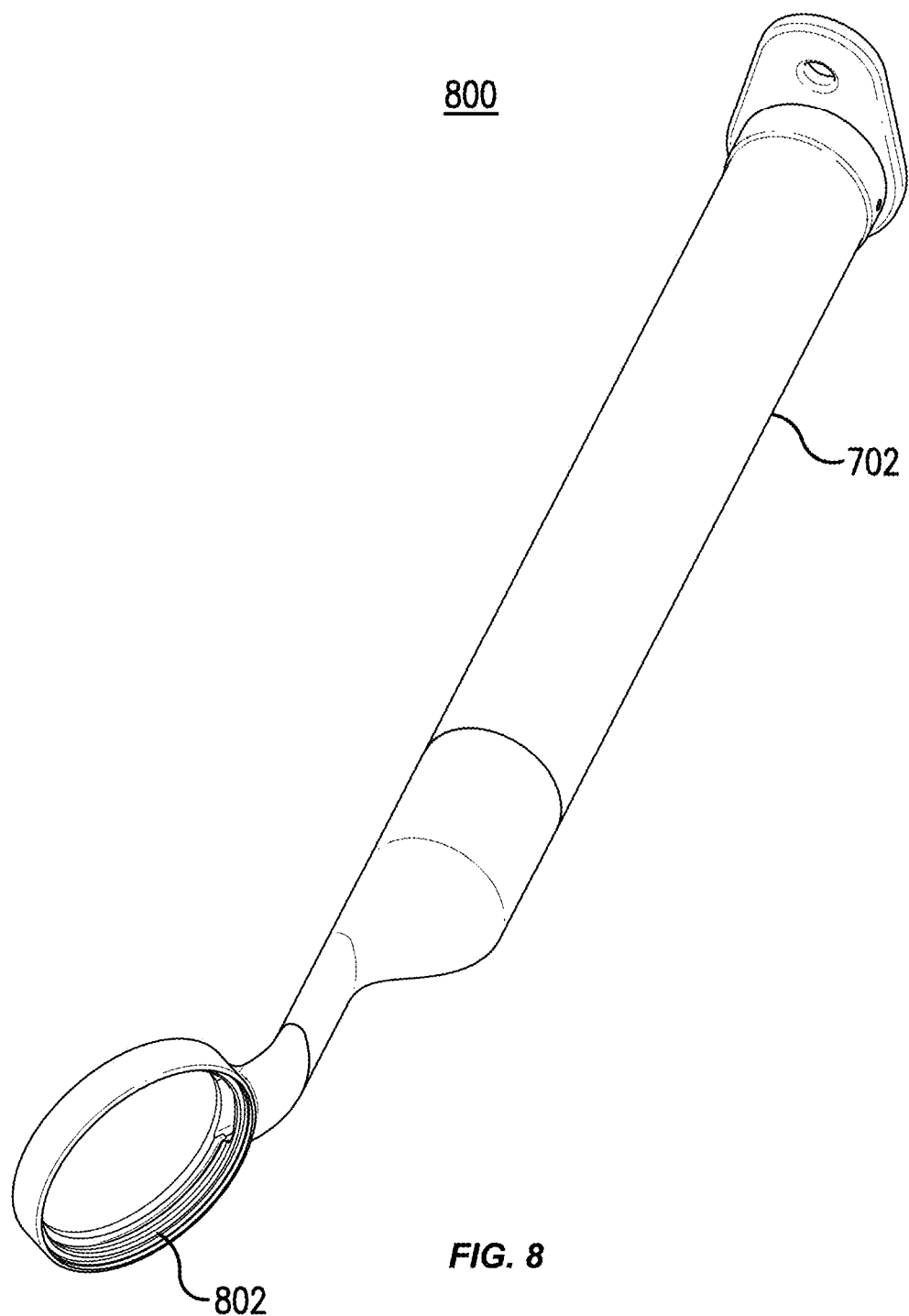
FIG. 8 illustrates a perspective diagram of a shell for a head portion of a dental mirror.

Mirror head 704 in layer 710 is configured to engage with a backing 744 and a gasket 742 in layer 740. Backing 744 includes threads configured to mate with threads on mirror head 704. Those threads are illustrated in FIG. 8. FIG. 8 illustrates a perspective diagram 800 of a shell for a head portion of a dental mirror. Diagram 800 shows threads 802 that are configured to mate with backing 744. Gasket 742 sits between backing 744 and threads 802 to create an airtight seal. In some embodiments, a sealant is also added while treading the components together to improve the sealing characteristics.

Returning to FIG. 7, between layers 710 and 740 are layers 720 and 730. Layer 730 include a printed circuit board (PCB) 734 that rests on backing 744. PCB 730 has an image sensor 732 and a plurality of light sources 736 arranged around a perimeter of PCB 734. PCB 734 also has some control circuitry and a connector 738.

Image sensor 732 captures still or video digital images. In some embodiments, image sensor 732 is an image sensor, or plurality thereof, that includes a pixel array, such as a charged coupled device (CCD), or a complementary metal-oxide-semiconductor (CMOS) sensor, or the like.

The plurality of light sources 736 illuminates objects in the proximity of dental instrument 156. In some embodiments, light sources 736 illuminate areas of a person's mouth to improve the image reflected in viewfinder mirror 103 or captured by image sensor 732. In some embodiments, a plurality of light sources 736 are included. In some embodiments, light sources 736 emits light. In some embodiments, light sources 736 transmit light emitted elsewhere in dental instrument 156. In some embodiments, the intensity of the light emitted or transmitted by light sources 736 can be controlled. In some embodiments, the intensity of illumination by a plurality of light sources 736 is concurrently controlled. In some embodiments, the intensity of each light sources 736 of a plurality of light sources 736 is independently controlled. In some embodiments, a plurality of light sources 736 all emit or transmit the same or similar light wavelengths (or colors). In some embodiments, different wavelengths (or colors) may be emitted or transmitted by a plurality of light sources 736. In some embodiments, each light source 736 is a led emitting diode (LED). In some embodiments, each light source 736 is a light pipe, such as an optical fiber cable or the like. In some embodiments, each light source 736 is a monochromatic light (a laser).

Connector 738 receives signals to control the plurality of light sources 736.

Layer 720 rests on top of layer 730 and includes a light diffuser 726, mirror support 724 and lens protector 722.

Light diffuser 726 scatters light to soften light emitted from light sources 736. Light diffuser 726 may include a translucent material such as ground glass, teflon, opal glass, or greyed glass.

Mirror support 724 provides structural support for reflective surface 101. Adhesive may be applied between mirror support 724 and reflective surface 101. Mirror support 724 may stiffen reflective surface 101 and make reflective surface 101 more resistant to fracture.

Lens protector 722 is an opaque construct made out of silicone or other materials that can sustain temperatures of an autoclave. Lens protector 722 allows light from outside that is to be directed towards the pass-through 708 to enter image sensor 732. Lens protector 722 operates to block "light pollution." This reduces the light noise that may be wrongly reflected to the image sensor 732. Lens protector 722 may also include a lens, a transmissive optical device that focuses a light by means of refraction to form an image for detection by image sensor 732. The lens may be a simple lens or compound lens. It may be made of a transparent material such as glass or plastic.

As mentioned above, dental instrument 156 may be at least part of a smart dental mirror. Dental instrument 156 may be autoclavable or may include components of the smart dental mirror that are autoclavable. Components of the smart dental mirror that are not autoclavable may be included in a separate piece, which may be called a streamer portion. Because this streamer portion is not to be autoclaved, it may be positioned on the smart dental mirror such that it does not make contact with the patient's mouth when used by the healthcare provider.

Figure 9:
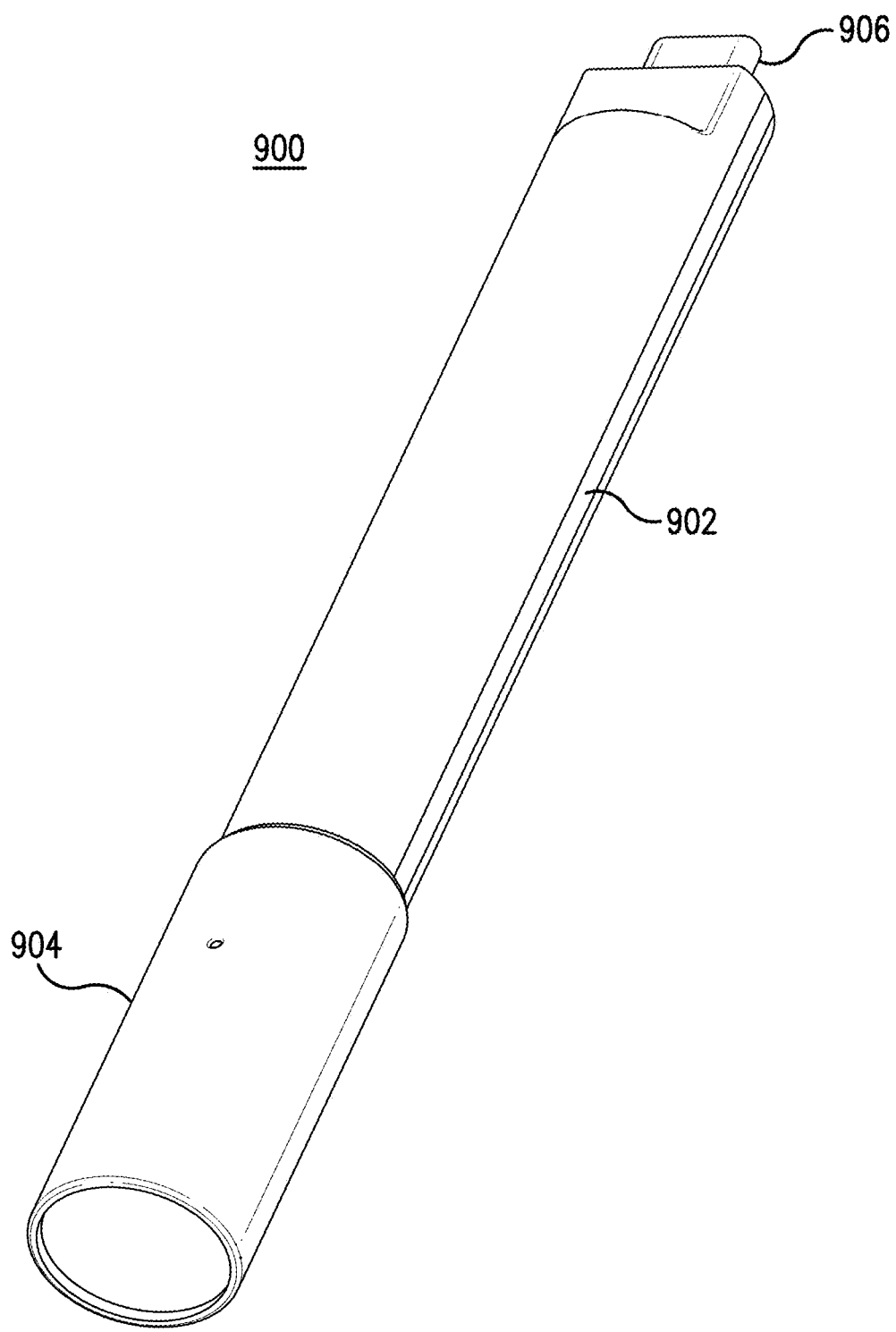
FIG. 9 illustrates a streamer portion of a dental mirror.

FIG. 9 illustrates a streamer 900 of a dental mirror. Streamer 900 includes a connector 906, a shell 902, and a shell 904. Connector 906 is configured to electrically and communicatively connect to dental instrument 156. In some embodiments, Shell 902 is shaped to be inserted into cavity 158 of dental instrument 156. Shell 904 may enclose a wireless antenna and may be made of materials that are permeable to electromagnetic signals.

Figure 10:
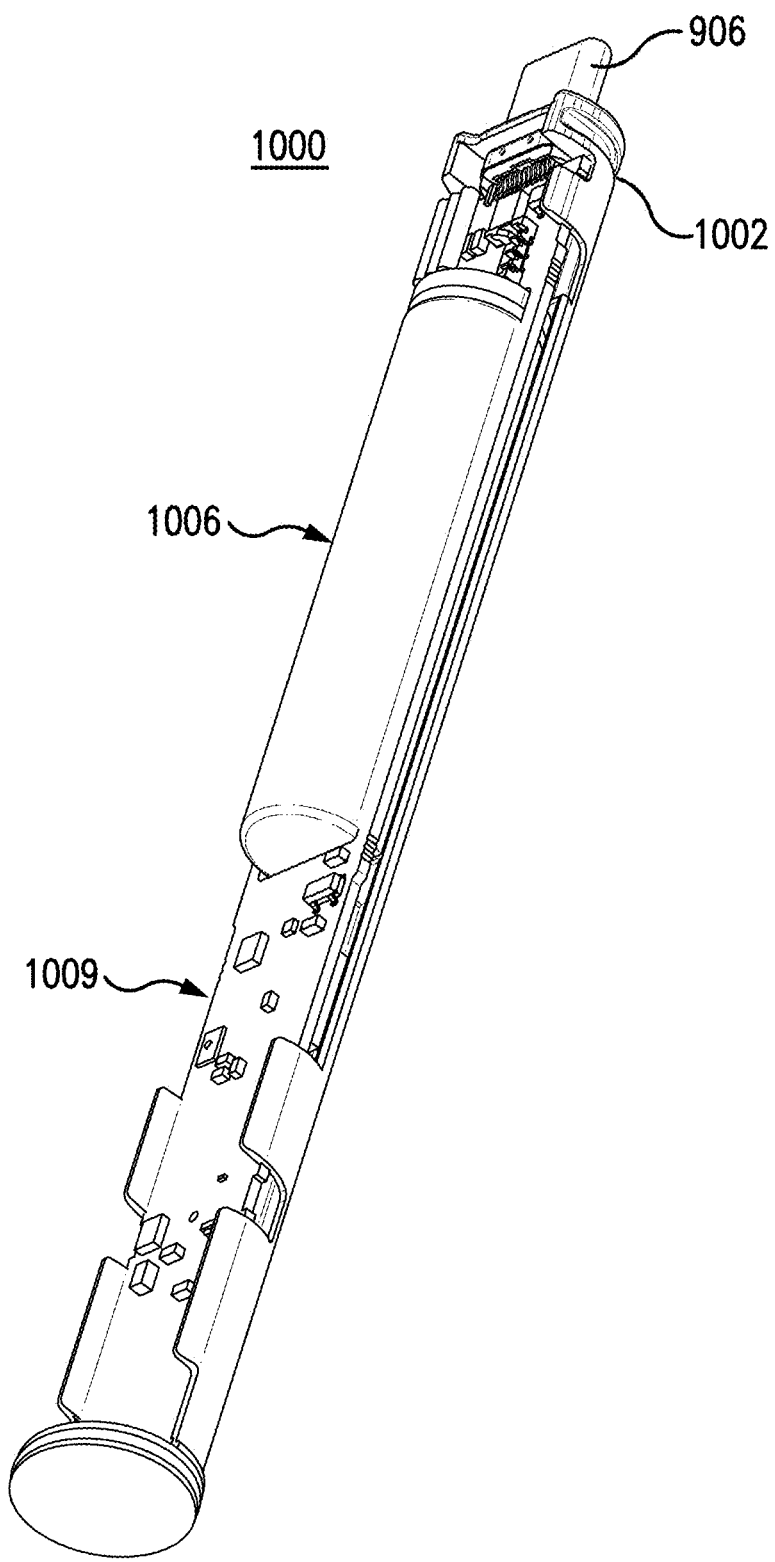
FIG. 10 illustrates the streamer portion with an outer shell removed.

FIG. 10 includes a diagram 1000 that illustrates the streamer portion with an outer shell removed. Diagram 1000 illustrates a tray 1002 that contains a PCB 1004. As discussed below, PCB 1009 includes a power subsystem 1006, a processor and memory. It also includes a wireless antenna and a connector to dental instrument 156 or a power charger or a base station.

Figure 11:
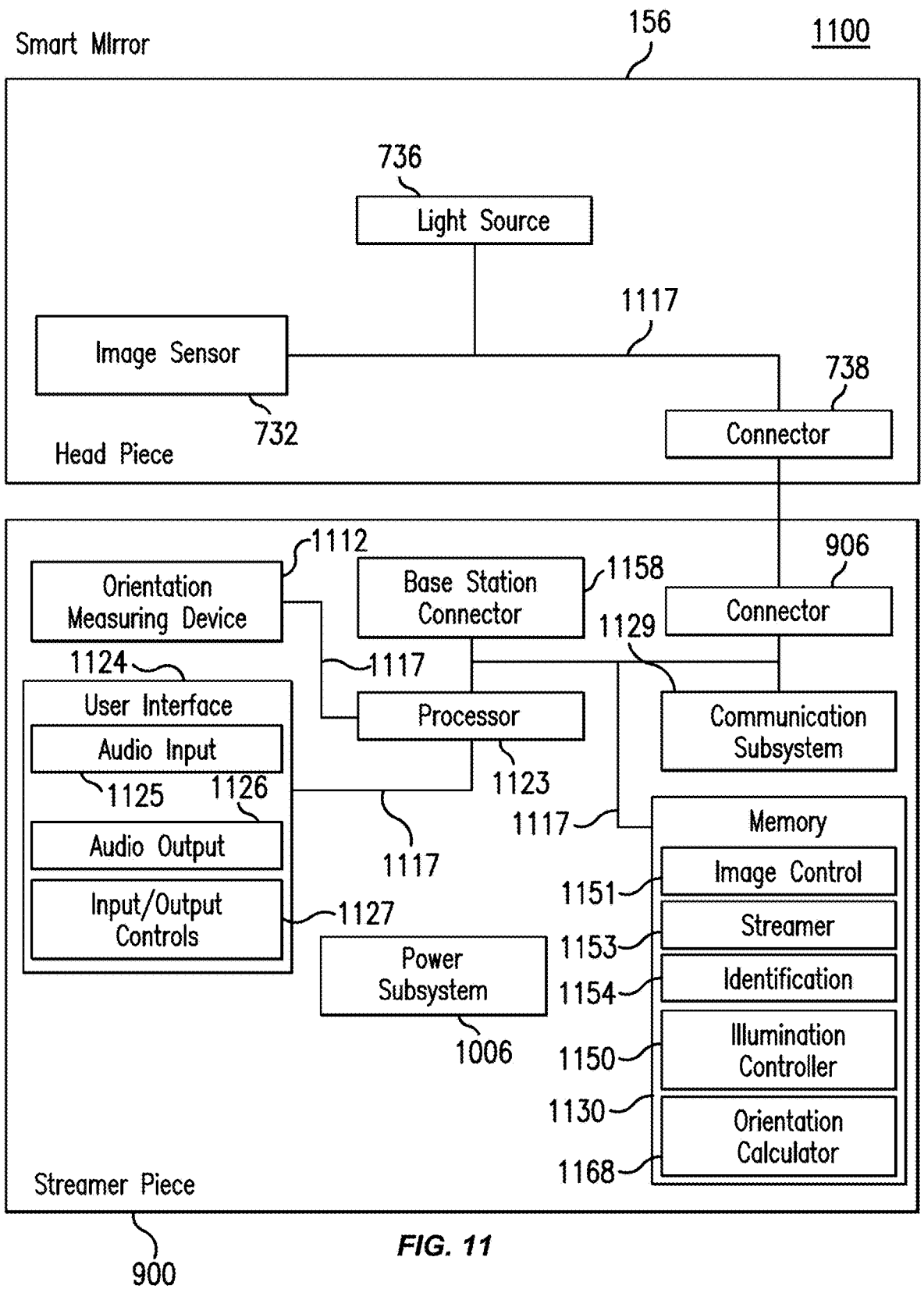
FIG. 11 illustrates a block diagram of a smart dental mirror.

FIG. 11 illustrates a block diagram of a smart mirror device 1100. As discussed above, smart mirror device 1100 has two separable components, dental instrument 156 (the head piece for insertion into the oral cavity) and streamer 900, and dental instrument 156 includes image sensor 732, light source(s) 736, and a connector 738.

It may be appreciated for those skilled in the art that a plurality of signal lines or buses 1117 may exist, thus different components may be linked by different signal lines or buses 1117, and that the signal lines or buses 1117 depicted in the schematic diagram may represent a plurality of such.

As discussed above for FIG. 1, viewfinder mirror 103 is a mirror, thus having a reflective area. The reflection from viewfinder mirror 103 provides visual guidance to a user about the objects that may be included in images captured by image sensor 732. As mentioned above, viewfinder mirror 103 may be round. In some embodiments, viewfinder mirror 103 is planar. In some embodiments, viewfinder mirror 103 is curved, concave, or convex. In some embodiments, viewfinder mirror 103 has a spherical shape. In some embodiments, viewfinder mirror 103 has a rectangular shape. It can be appreciated by those skilled in the art that smart mirror device 1100 can be embodied with different shapes of viewfinder mirror 103 and/or a plurality of viewfinder mirror 103 without departing from the spirit of this invention.

Connector 738 of dental instrument 156 connects (physically and/or electronically) to connector 906 of streamer 900. Connector 906 may be a USB terminal. Image sensor 732 and light source 736 receive electrical power from streamer 900 through connector 738. In addition, control and signaling is passed to and from streamer 900 and light source 736 through connector 738. For example, image sensor 732 may transmit images captured via bus 1117 to connector 738, which transmits images to streamer 900. Similarly, connector 738 may receive and pass along control information indicating when and whether to activate image sensor 732. For light sources 736, connector 738 may receive commands which cause light sources 736 to activate and determine when and how to activate them. Connector 738 is adapted to connect to a connector 906 in streamer 900.

Turning to streamer 900, streamer 900 includes an orientation measuring device 1112, a user interface 1124, a processor 1123, a base station connector 1158, connector 906, communication subsystem 1129, power subsystem 1121, and a memory 1130.

Base station connector 1158 enables streamer 900, which may or may not be attached to dental instrument 156, to dock with a base station. The docking may occur through a physical connection which holds streamer 900 at a predefined orientation. In addition, the docking may occur through a USB or near field communication connection or the like. When docking with the base station, streamer 900 may receive electrical power through base station connector 1158, which may be used to charge power subsystem 1006. In addition, streamer 900 may receive control and signaling information through base station connector 1158. For example, base station connector 1158 may receive information needed to configure a wireless communication connection between streamer 900 and the base station. Base station connector 1158 may provide the wireless configuration information (such as a service set identifier and password) to communication subsystem 1129, as is discussed below. And, when docked to a base station, base station connector 1158 may signal orientation measuring device 1112 or software in memory 1130 to calibrate. In some embodiments, connector 906 may integrated into base station connector 1158.

Power subsystem 1006 stores power for smart mirror device 1100 and provides power to the other components of smart mirror device 1100. Power subsystem 1121 may include batteries, such as AAAA batteries, or a capacitor.

Orientation measuring device 1112 measures an orientation (including x,y,z, position and yaw, pitch, roll direction) of viewfinder mirror 103 or generates data that enables it to calculate an orientation of viewfinder mirror 103. In some embodiments, orientation measuring device 1112 is an accelerometer. An example of an accelerometer is MMA8453Q available from NXP Semiconductors N.V. of Eindhoven, Netherlands. In some embodiments, orientation measuring device 1112 is a gyroscope. An example of an orientation measuring device 1112 is FXAS21002C also available from NXP Semiconductors N.V. The gyroscope could also be a compound device such as a TDK invensense.

User interface 1124 includes an audio input 1125, audio output 1126, and input/output controls 1127. Audio input 1125 captures audial information. In some embodiments, audio input 1125 includes a microphone. In some embodiments, audio input 1125 captures human voice, for example, to enable a healthcare provider to dictate observations for a patient's medical record. Streamer 900 includes an audio output 1126, which emits sounds. In some embodiments, audio output 1126 includes one or more speakers or buzzers. In some embodiments, audio output 1126 includes headphone jacks and/or headphones.

Input/output controls 1127 can include buttons, lights, knobs, capacitive sensors, actuators for haptic feedback or the like for a user to control and/or receive feedback relating to processes in smart mirror device 1100, for example, to initiate audio recording or image capturing, or set an intensity of illumination.

Communication subsystem 1129 allows streamer 900 to connect to one or more remote computational devices, including, for example, to a base station, or to a general purpose computational device such as personal computer, a smart phone, a tablet or similar, or a specialized computational device such as to another smart mirror device or remote speakers or the like. In some embodiments, communication subsystem 1129 is adapted to connect to a wireless network, including, but not limited to, WiFi and/or Bluetooth. In some embodiments, communication subsystem 1129 is adapted to attach to a wired network, including, but not limited to, Ethernet, USB or thunderbolt.

In an embodiment, the smart mirror device may be shipped with a sticker with a visual code, such as a QR code, printed thereon. A smart phone or tablet computing device can scan the QR code and to determine as SSID/Password to connect to a WiFi network hosted from communication subsystem 1129. In this way, the tablet computing device can communicate with the smart mirror device and receive video captured from the smart mirror device.

Memory 1130 may include random access memory (RAM) and may also include nonvolatile memory, such as read only memory (ROM) and/or flash memory. Memory 1130 may be embodied as an independent memory component, and may also be embedded in another component, such as processor 1123 and/or image sensor 732, or may be embodied as a combination of independent as well as embedded, and/or a plurality of memory components. Memory 1130 is adapted to include software modules (a module is a set of instructions). In particular, memory 1130 includes a streamer module 1153, identification module 1154, illumination controller module 1150, image control module 1151, and orientation calculator module 1168.

Processor 1123 is adapted to run instructions stored in memory 1130. Processor 1123 may be a micro-controller unit (MCU), a digital signal processor (DSP) and/or an Image/Video Processing unit or like components that run instructions. An example of an MCU is MSP432P401x available from Texas Instruments Inc. of Dallas, Texas. An example of a DSP is C5000 available from Texas Instruments Inc. of Dallas, Texas. An example of an image/video processor is OMAP3525 also available from Texas Instruments Inc. of Dallas, Texas Another example of the processor is the FPGA, such as the one available from Xilinx. One or more processor 1123 may be present. Processor 1123 may be an independent component, it may also be embedded in another component, such as in image sensor 732, orientation measuring device 1112, or any combination thereof. Each subcomponent may also have internal memory devices.

Illumination controller module 1150 controls the operation of light source 736. In some embodiments, illumination controller module 1150 sets the intensity of illumination of light source 736. In some embodiments, illumination controller module 1150 receives a user request to increase or reduce illumination. In some embodiments, illumination controller module 1150 receives a user request to turn on or off some or all of light source 736. In some embodiments, illumination controller module 1150 receives requests from other software modules to increase and/or decrease illumination of one or more of light source 736. In some embodiments, user input as well as said requests are used to determine an intensity of illumination.

Orientation calculator module 1168 reads data from orientation measuring device 1112. Orientation calculator module 1168 may for example integrate data from a gyroscope and accelerometer to determine a location (in, for example, x,y,z coordinates) and a direction (for example, yaw, pitch, and roll). Because orientation calculator module 1168 uses integration to determine the location and direction of smart mirror device 1100, errors from the gyroscope and the accelerometer can accumulate over time. However, as described above, base station connector 1158 may dock with the base station in such a way to position streamer 900 at a known angle. When base station connector 1158 is docked with the base station, base station connector 1158 may signal orientation calculator module 1168 to calibrate. To calibrate, orientation calculator module 1168 may set the x, y, z, and yaw, pitch, and roll values to fixed values, such as the value zero. Thus, when streamer 900 is moved around, the coordinate and direction values orientation calculator module 1168 determines values which may be relative to the coordinate and direction values set at the base station.

Image control module 1151 controls the capture of images and video, and affects the output image quality. In some embodiments, image control module 1151 controls the intensity of illumination, for example, by requests to illumination controller module 1150, for example, to improve the illumination conditions for a better image capture quality. In some embodiments, image control module 1151 processes a set of time-successive images to create a single output image which has an improved visual quality, for example, but not limited to by selecting one image out of the set, or by combining portions of images, each portion from an image in the set. In some embodiments, values indicating the acceleration of image sensor 732 when an image was captured are used to improve the quality of an output image, for example, but not limited to, selecting images with least acceleration or interpolating among portions of two or more images of different acceleration. In some embodiments, image control module 1151 controls the aperture and/or focal point of a lens. In some embodiments, image control module 1151 triggers the capture of a sequence of images each with a different illumination. In some embodiments, image control module 1151 triggers the capture of a sequence of images each with a possibly different group of one or more of light sources 736 set to illuminate, while the other one or more of light source 736 are set to not illuminate. In some embodiments, image control module 1151 rotates an image, for example based on a rotation value generated by orientation calculator module 1168.

Identification module 1154 identifies smart mirror device 1100 to a remote computational device. In some embodiments, identification module 1154 implements an authentication handshake protocol in which the identification occurs over a network session. In some embodiments, identification module 1154 couples an identification to data prior to the data being transferred to a remote computational device. The identification may include a globally unique ID for streamer 900. It may also be timestamped and digitally signed.

Streamer module 1153 prepares and/or streams data to a remote computational device. The data can include video collected from image sensor 732, smart mirror device 1100's orientation and location collected from orientation calculator module 1168, audio input collected from audio input 1125, any data collected from input/output controls 1127, power related data collected from power subsystem 1006 and the specification of how light source 736 is illuminated from illumination controller module 1150. Streamer module 1153 may associate data collected from these various sources with each other. To associate data collected from different sources, streamer module 1153 may attach a timestamp. For example, each frame in video image sensor 732 may include a timestamp which is collected. Similarly, the orientation, audio, power, and input control information may have a timestamp indicating when that information was collected, and the illumination information may have a timestamp indicating when light source 736 was illuminated in the manner specified.

In some embodiments, streamer module 1153 formats images, video, audio and other data in a format for streaming to an application executing on a remote computational device via communication subsystem 1129. In some embodiments, streamer module 1153 formats images, video, audio and other data in a format suitable for streaming to an Internet browser, for example, but not limited to, HTTP streaming, HTML, HTML5, RTSP, WebRTC. In some embodiments, streamer module 1153 formats images, video, audio and other data with compression formats and/or format containers such as, but not limited to, JPG, JPG 2000, MPEG-4, H.264, H.265, AAC, PCM, G.711, G.726, and the like. In some embodiments a proprietary format is used, the invention is not so limited.

Estimation terms, such as "approximate," "approximately," "about," and the like may be used herein to indicate the value of a given quantity that may vary based on a particular technology and/or certain parameter(s). For example, the estimation term may modify amounts, sizes, formulations, parameters, and other quantities and characteristics, and need not be exact, but may be approximate and/or larger or smaller, as desired, reflecting tolerances, conversion factors, rounding off, measurement error and the like, and other factors known to those of skill in the art. Such estimation terms may indicate a value of a given quantity that varies within, for example, 0-10% of the value (e.g., ±0.5%, ±5%, or ±10% of the value).

Directional and spatially relative terms, such as "inner," "outer," "proximal," "distal" and the like, may be used herein for ease of description to describe one element or feature's relationship to another element(s) or feature(s) as illustrated in the figures. The directional and spatially relative terms are intended to encompass different orientations of the device in use or operation in addition to the orientation depicted in the figures. The apparatus may be otherwise oriented (rotated 90 degrees or at other orientations) and the directional and spatially relative descriptors used herein may likewise be interpreted accordingly.

As used herein, the singular forms "a," "an" and "the" include plural referents unless the context clearly dictates otherwise. Thus, for example, reference to "a" component includes aspects having two or more such components, unless the context clearly indicates otherwise.

It is to be understood that the phraseology or terminology herein is for the purpose of description and not of limitation such that the terminology or phraseology of the present specification is to be interpreted by those skilled in relevant art(s) in light of the teachings herein.

The embodiment(s) described, and references in the specification to "one embodiment," "an embodiment," "an example embodiment" and the like indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A method for sterilizing an intraoral mirror, comprising:
    inserting a plug into a cavity in the intraoral mirror, the plug configured to engage the cavity;
    sterilizing the intraoral mirror; and
    removing the plug from the intraoral mirror.

2. The method of claim 1, wherein the sterilization occurs in an autoclave.

3. The method of claim 1, wherein the plug permits gas to flow from the cavity through a valve when a pressure inside the cavity is greater than a pressure in an environment outside the cavity.

4. The method of claim 1, wherein the plug prevents gas from flowing into the cavity through a valve when a pressure in an environment outside the cavity is greater than a pressure inside the cavity.

5. The method of claim 1, wherein the plug prevents at least one of particles, steam, and contaminants from entering the cavity.

6. The method of claim 1, wherein the intraoral mirror comprises a printed circuit board, the printed circuit board disposed in the cavity.

7. A method for controlling pressure with a plug in a dental instrument during sterilization, comprising;
plugging a cavity in the dental instrument;
permitting gas to flow from the cavity through a valve in the plug when a pressure inside the cavity is greater than a pressure in an environment outside the cavity;
preventing gas from flowing into the cavity through the valve in the plug when the pressure in the environment outside the cavity is greater than the pressure inside the cavity; and
unplugging the cavity.

8. The method of claim 7, the plug comprising:
a hollow housing having a distal and a proximal end, the proximal end configured to engage the cavity of the dental instrument; and
the valve,
wherein the valve permits gas to flow from the cavity of the dental instrument when the pressure outside the cavity decreases, and
wherein the valve prevents gas from flowing into the cavity of the dental instrument when the outside pressure increases.

9. The method of claim 7, wherein the dental instrument is sterilized in an autoclave.

10. The method of claim 7, wherein the dental instrument is an intraoral mirror.

11. The method of claim 7, wherein the dental instrument comprises a printed circuit board, the printed circuit board disposed in the cavity.

12. The method of claim 7, wherein the plug prevents particles, steam, or contaminants from entering the cavity.

13. A plug for use with a dental instrument during sterilization, the plug comprising:
a hollow housing having a distal and a proximal end, the proximal end configured to engage a cavity of the dental instrument; and
a valve,
wherein the valve permits gas to flow from the cavity of the dental instrument when a pressure outside the cavity decreases, and
wherein the valve prevents gas from flowing into the cavity of the dental instrument when the outside pressure increases.

14. The plug of claim 13, wherein the valve comprises a sealing member coupled to a piston rod, the piston rod biased in the proximal direction by a spring.

15. The plug of claim 13, further comprising an indicator, the indicator configured to indicate a pressure difference between the outside pressure and a pressure in the cavity.

16. The plug of claim 15, wherein the indicator is coupled to a sealing member.

17. The plug of claim 15, wherein the indicator indicates the pressure difference between the outside pressure and the pressure in the cavity by being located at one of a first and a second position.

* * * * *